United States Patent [19]

Bäbler

[11] Patent Number: 4,550,215

[45] Date of Patent: Oct. 29, 1985

[54] PROCESS FOR THE PREPARATION OF PERYLENE

[75] Inventor: Fridolin Bäbler, Marly, Switzerland

[73] Assignee: Ciba Geigy Corporation, Ardsley, N.Y.

[21] Appl. No.: 594,144

[22] Filed: Mar. 28, 1984

[30] Foreign Application Priority Data

Apr. 8, 1983 [CH] Switzerland .................. 1898/83

[51] Int. Cl.$^4$ .................................... C07C 1/20
[52] U.S. Cl. ............................................ 585/469
[58] Field of Search .................... 585/469, 25, 26

[56] References Cited

U.S. PATENT DOCUMENTS 3,132,187  5/1964  Turetzky ..................... 585/469

FOREIGN PATENT DOCUMENTS 486491  11/1929  Fed. Rep. of Germany.
46-21863  6/1971  Japan.

OTHER PUBLICATIONS

G. M. Badger et al., J. Chem. Soc. 1957, 4417.
R. Scholl et al., Chem. Ber. 43, 2202, (1910).
S. Iwashima et al., Bull. Chem. Soc. Japan, 41, 2789, (1968).

*Primary Examiner*—D. E. Gantz
*Assistant Examiner*—Chung K. Pak
*Attorney, Agent, or Firm*—Luther A. R. Hall

[57] ABSTRACT

A process for the preparation of perylene by heating perylenecarboxylic acids or the anhydrides or salts thereof, in the presence or absence of metal oxides, metal hydroxides or metal carbonates, to temperatures in the range from 380° to 550° C., which process is carried out under normal or slightly reduced pressure and the perylene so obtained is removed from the reaction vessel with a stream of inert gas. The perylene so obtained is of high purity.

9 Claims, No Drawings

PROCESS FOR THE PREPARATION OF PERYLENE

The present invention relates to a process for the preparation of perylene by decarboxylation of perylenetetracarboxylic acid or derivatives thereof.

Perylene can be prepared by a variety of methods, most of which, however, afford only low yields. For example, perylene was obtained in a yield of 1% by G. M. Badger et al. by dehydrocyclising naphthalene with AlCl$_3$ as catalyst (*J. Chem. Soc.* (1957), 4417) and in a yield of 10% by R. Scholl et al., starting from 1,1'-binaphthyl (Chem. Ber. 43, (1910), 2202).

German Pat. No. 486 491 describes a process in which perylene is obtained in good yield by decarboxylation of perylenecarboxylic acids, or salts or derivatives thereof, in 12% aqueous potassium hydroxide solution, by heating to 250° C. for several hours in an autoclave. However, the perylene so obtained has a high content of impurities and must be subjected to a subsequent purification process. A further drawback of this process is the necessity of having to use very expensive special autoclaves.

According to Japanese published patent specification No. JA-71 21863, perylene is obtained by thermolysis of perylenetetracarboxylic acid, or a derivative thereof, in the presence of soda lime, at about 440° C. under reduced pressure. Owing to its lack of purity, the perylene obtained by this process must also subsequently be recrystallised and purified over alumina. Sublimation under reduced pressure has the further disadvantage that impurities may be entrained. In addition, it is necessary to employ special apparatus in the temperature range from 400° to 500° C. and under pressures of $10^{-5}$ to $10^{-11}$ bar.

Accordingly, the present invention relates to a process for the preparation of perylene by heating perylenetetracarboxylic acid, or an anhydride or a salt thereof, in the presence or absence of a metal oxide, metal hydroxide or metal carbonate, to temperatures in the range from 380° to 550° C., preferably from 400° to 460° C., under normal or only slightly reduced pressure, and removing the perylene so obtained from the reaction vessel with a stream of inert gas.

Suitable starting materials are perylenemono-, -di-, -tri- or -tetracarboxylic acids and salts thereof, for example the sodium, potassium, calcium or magnesium salts. The preferred starting material, however, is perylenetetracarboxylic dianhydride.

Examples of suitable metal compounds which promote the formation of perylene are alkaline earth metal oxides and ZnO, the carbonates and hydroxides thereof, as well as aluminium oxide and aluminium hydroxide, individually or in admixture. Particularly suitable metal compounds are alkali metal hydroxides and alkaline earth metal hydroxides, and alkaline earth metal oxides, individually or in admixture, for example soda lime, as these metal compounds make possible the formation of perylene at temperatures below 480° C.

It s preferred to use 1 to 6 parts, most preferably 1.5 to 3.5 parts, of metal compound to 1 part of perylenetetracarboxylic acid or derivative thereof. It is advantageous to mix the reactants intimately before heating. This is done e.g. in mixers or by grinding, for example in a ball mill, bead mill, or some other grinding mill.

The preferred alkaline earth metal oxides may be mixed in the dry state, in a high-speed mixer, with the perylenetetracarboxylic acid or derivative thereof. Magnesium oxide is conveniently ground with peryleneteracarboxylic dianhydride in water. Upon removal of the water, a homogeneous mixture of MgO, Mg(OH)$_2$, magnesium salt and anhydride of perylenetetracarboxylic acid is obtained.

The starting materials are heated in a stream of inert gas. For economic reasons the preferred inert gas is nitrogen. Other inert gases may also, of course, be used. The process is conveniently carried out at pressures higher than 0.7 bar (1 bar = $10^6$ dyne/cm$^3$), preferably at atmospheric pressure.

Depending on the nature of the metal compound employed. the reaction time is from one hour to several hours. The perylene so obtained is advantageously carried, in the gaseous state, by the inert gas into a receiving vessel outside the heating zone. Immediately on leaving the heating zone, the perylene changes from the gaseous into the solid state and is precipitated in the form of a yellow powder in the receiving vessel. Depending on the speed of the inert gas, the perylene is obtained in the form of fine or course crystals. The presence of water, originating from the metal hydroxides, in the heating phase and at the the start of the reaction does not interfere with the formation of perylene.

The perylene obtained by the process of this invention is of high purity and need neither be subsequently sublimed nor recrystallised in organic solvents.

It is surprising that perylene can be obtained in good yield and very high purity by the process of the invention under normal pressure and at temperatures of 460° C. and below.

Perylene is a very stable polycyclic aromatic hydrocarbon which has recently attained great importance because of its special physical properties. It is of crucial importance that perylene should have a high degree of purity.

Of the many uses of perylene, mention may be made of the following: the use of perylene for the preparation of electrophoretic toners (JA patent application No. 82-222 247; priority of 15.7.1980)
blue electroluminiscent films (P. S. Vincett at al., *Thin Solid films* 94 (1982) 171–183)
photosensitive systems (U.S. Pat. No. 3,729,313, priority of 6.12.71)
electrically highly conductive compounds (P. Koch et al., *Mol. Crist. Liq. Crist.* 86 (1–4), 1982, 1827–41)
charge transfer complex compounds, for example with iodine (Cobb, Wallis, *J. Phys. Chem.* 72, 1968, 1968, 2992) or with 1,3,5-trinitrobenzene (Orchin, Friedel, *J. Am. Chem. Soc.* 68, 1946, 573).

In the following Examples parts are by weight, unless otherwise stated.

EXAMPLE 1

52 parts of magnesium oxide and 28 parts of perylenetetracarboxylic dianhydride are suspended in 550 parts of water in a glass bead mill and the suspension is thoroughly ground with 1900 parts of glass beads (diameter: 4.5 to 5 cm) for 4½ hours at a speed of 320 rpm while cooling externally with water. The glass beads are then separated from the suspension and washed with a small amount of water. The suspension is filtered and the filter cake is dried, without being washed, in a vacuum cabinet at 80°–90° C. and pulverised.

Yield: 91 parts of a mixture consisting of MgO, Mg(OH)$_2$, and the magnesium salt and anhydride of perylenetetracarboxylic acid. Analysis shows that the content of perylenetetracarboxylic dianhydride is about 27%.

28.5 parts of the above mixture are heated to 460° C. in a glass vessel under a constant stream of nitrogen. The nitrogen is passed from the reaction vessel to a receiving vessel which is outside the heating zone. As soon as the temperature of the reaction mixture has reached about 150° C., steam forms and is entrained by the inert gas. After about 10 minutes at 460° C., perylene evolves and is entrained by the inert gas together with water and CO$_2$, and precipitates as a yellow solid in the receiving vessel. After a further 45 minutes only perylene is removed from the reaction vessel by the inert gas. Nitrogen is passed through the reaction vessel at 460° C. until there is no further evolution of perylene. The perylene is then freed from any water still present at 80° C. in a drying cabinet.

Yield: 3.2 g of yellow perylene with a melting point of 278° C. and of high purity (confirmation by spectrographic analysis). The yield is 65%, based on perylenetetracarboxylic dianhydride.

EXAMPLE 2

30 parts of perylenetetracarboxylic dianhydride and 100 parts of soda lime (a mixture of NaOH and Ca(OH)$_2$) are thoroughly mixed for a few minutes in an Osterizer laboratory mixer, whereupon the colour of the perylenetetracarboxylic dianhydride changes from red to olive green. The mixture is heated to 445° C. in a glass vessel under a constant stream of nitrogen over the course of 1½ hours. The nitrogen is passed through the reaction vessel and then through a receiving vessel which is outside the heating zone. During the heating phase, a small amount of steam is removed by the inert gas. Perylene is formed after about 15 minutes at 440°–445° C. and is carried by the inert gas to the receiving vessel. Nitrogen is passed through the reaction vessel at 440°–445° C. until the formation of perylene has ceased. The perylene collected in the receiving vessel is freed from any traces of water still present at 80° C. Yield: 15.5 g of perylene with a melting point of 278°–279° C. The yield is 80%, based on a perylenetetracarboxylic dianhydride.

The absorption spectrum of the perylene so obtained has a molar extinction coefficient of log $\epsilon = 4.532$ in dimethylformamide at $\lambda_{max}$ 435 nm.

EXAMPLE 3

The procedure of Example 2 is repeated, passing nitrogen under slightly reduced pressure through the reaction vessel and subsequently into the receiving vessel outside the heating zone. Perylene is obtained in correspondingly good yield and quality.

What is claimed is:

1. A process for the preparation of perylene by heating a perylenecarboxylic acid or an anhydride or salt thereof, in the presence or absence of a metal oxide, metal hydroxide or metal carbonate, to temperatures in the range from 380° to 550° C., which process is carried out under a pressure above 0.7 bar and the perylene so obtained is removed from the reaction vessel with a stream of inert gas.

2. A process according to claim 1, wherein the starting material is perylenetetracarboxylic dianhydride.

3. A process according to claim 1, wherein the metal oxide is aluminium oxide, zinc oxide, an alkali metal oxide or alkaline earth metal oxide, individually or in admixture.

4. A process according to claim 1, wherein the metal oxide is calcium or magnesium oxide, individually or in admixture.

5. A process according to claim 1, wherein the metal hydroxide is aluminium hydroxide or an alkali metal hydroxide or alkaline earth metal hydroxide, individually or in admixture.

6. A process according to claim 1, wherein the metal hydroxide is potassium hydroxide, sodium hydroxide, magnesium hydroxide or calcium hydroxide, individually or in admixture.

7. A process according to claim 6, wherein the metal hydroxide is soda lime.

8. A process according to claim 1, wherein the reaction temperature is in the range from 400° to 460° C.

9. A process according to claim 1, wherein the reaction is carried out under atmospheric pressure.

* * * * *